United States Patent [19]

Klocke et al.

[11] Patent Number: 4,960,791

[45] Date of Patent: Oct. 2, 1990

[54] SALANNIN DERIVATIVE INSECT CONTROL AGENTS

[75] Inventors: James A. Klocke, Salt Lake City, Utah; Ronald B. Yamasaki, Sebastopol, Calif.

[73] Assignee: NPI, Salt Lake City, Utah

[21] Appl. No.: 285,757

[22] Filed: Dec. 16, 1988

[51] Int. Cl.$^5$ .................. A61K 31/34; C07D 307/93
[52] U.S. Cl. .................................. 514/468; 549/456
[58] Field of Search ..................... 549/456; 514/468

[56] References Cited

PUBLICATIONS

Henderson et al., Tet., 24, pp. 1525–1528 (1968).
Kraus et al., Liebigs Ann. Chem., pp. 181–189 (1981).
Rojatkar et al., Phytochemistry, 28(1), pp. 203–205 (1988).

*Primary Examiner*—Mary C. Lee
*Assistant Examiner*—Bernard J. Dentz

[57] ABSTRACT

Derivatives of salannin, including 2′,3′,20,21,22,23-hexahydro salannin and 20,21,22,23-tetrahydro salannin derivatives, having up to 40-fold greater insect antifeedant activity than native salannin.

28 Claims, No Drawings

SALANNIN DERIVATIVE INSECT CONTROL AGENTS

FIELD OF THE INVENTION

The field of the invention is insect pest control. More specifically, it relates to a naturally occurring insect antifeedant compound and derivatives of it.

BACKGROUND

The need to develop new chemical insect control agents that are safe, selective, biodegradable, and environmentally acceptable is widely recognized. Conventional pesticides may be toxic not only to pest insects, but also to beneficial insects and even to humans, due to their neurotoxic mode of action. In addition, the development of insect resistance and the environmental pollution due to the mass application of persistent synthetic pesticides have given rise to increased interest in alternate measures for the commercial control of insect pests. Alternatives can include the use of natural plant products, representing an immense array of chemical structure types, which may serve as sources of or models for pest control agents. The bioassay-guided investigation of higher plants, especially those observed to be resistant to insect attack in the field, can result in the detection and subsequent isolation and structure elucidation of potential pest control agents. Some natural plant products which have already been commercialized for use in insect control include the pyrethrins, rotenone, and nicotine and other alkaloids (Klocke, J.A. 1986. In "*Allelochemicals: Role in Agriculture, Forestry, and Ecology.*" Waller, G. (ed.) ACS Symposium Series 330, American Chemical Society, Washington, D.C.). The search continues for still other useful plant products that will exhibit a selective toxicity towards pests combined with minimal adverse ecological and environmental impacts. Such compounds could find widespread commercial application in the agricultural, greenhouse and home garden supply markets.

The present invention includes a process of producing safe and novel insect control agents related to the naturally occurring plant compound salannin. Salannin is an insect antifeedant which disrupts the feeding and growth of susceptible insects and has the formula shown as 1a in Formula I. Antifeedant compounds are attractive in insect control since they are "biorational compounds" (i.e., they usually involve species-specificity and are generally neither persistent nor toxic). Traditional antifeedants have not been able to compete with conventional insecticides because they have been more expensive to produce and are capable of controlling only a narrow range of insect pests. We believe that the salannin derivatives described and claimed herein have a wider spectrum of activity (i.e., discourage more species of insects from feeding), will be effective in lower doses than formerly available antifeedants, and will be less expensive to produce commercially.

The inventions disclosed are derived from the tetranortriterpenoid salannin. Salannin occurs naturally in at least four species of Meliaceae: *Azadirachta indica* A. Juss (neem) (Henderson et al., *Tetrahedron Lett.* 1964 3969–3974; Henderson et al., *Tetrahedron* 1968 24:1525–1528), *Melia dubia* Cav. (de Silva et al., *Phytochemistry* 1969, 8: 1817–1819), *Melia azedarach* L. (chinaberry) (Srivastava, *J. Nat. Prod.* 1986, 49:56–61) and *M. volkensii* Gürke (Rajab et al., *J. Nat. Prod.* 1988, 51:168–171). The structure of salannin was proposed by Henderson et al. in 1964, and it is related to that of another highly potent insect antifeedant (and metamorphosis disrupter), azadirachtin (Zanno et al., *J. Am. Chem. Soc.* 1975, 97, 1975–1977; Kraus, W., in *Chemistry and Biotechnology of Biologically Active Natural Products*, edited by Szantay et al., Proc. Second Int. Conf. (Budapest, 1983) Elsevier; Amsterdam, New York, 1984: pp. 331–345.

Salannin acts as an antifeedant against the house fly (*Musca domestica* L.), California red scale (*Aonidiella aurantii* (Maskell)), locust (*Loscusta* spp.), Egyptian cotton leafworm (*Spodoptera littoralis* (Boisd.)), spiny bollworm (*Earias insulana* (Boisd.)), and the cucumber beetles *Acalymma vittatum* (F.) and *Diabrotica undecimpunctata howardi* (Warthen et al. 1978 U.S. Dept. Agric., Sci and Educ. Adm., *Agric. Res. Results.* Northeast. Ser., No. 2, 11 p. Beltsville, MD.; Warthen, 1979. U.S. Dept. Agric., Sci. and Educ. Adm., *Agric. Rev. and Manuals,* Northeast. Ser., No. 4, ARM-NE-4, 21 p. Beltsville, Md.; Meisner et al. 1981. *Phytooarasitica* 9, 27–32; Reed et al. 1982. *J. Econ. Entomol.* 75, 1109–1113.). We have also found antifeedant activity of salannin against the Colorado potato beetle (*L. decemlineata*).

The hereafter described and claimed salannin-derived antifeedants are "biorational" (Djerassem C., et al. 1974. *Science* 186, 596–607.) chemicals that are of relatively high selectivity for certain insects, low mammalian toxicity and biodegradable.

Although the insect antifeedant activity of salannin is documented, little is known about its structure-bioactivity relationships. Described and claimed herein are a number of derivatives of salannin which have greater antifeedant activity than the naturally-occurring salannin compound. Our work to establish chemical structure-activity relationships of salannin and derivatives as antifeedant compounds has shown that, for example, hydrogenation to the 2',3',20,21,22,23-hexahydrosalannin derivative increased the antifeedant activity of salannin against *L. decemlineata* at least eight-fold (from >400 $\mu g/cm^2$ leaf disk to 25 $\mu g/cm^2$). Other derivatives show up to forty-fold greater activity over native salannin.

SUMMARY OF THE INVENTION

Derivatives of salannin, a naturally occurring insect antifeedant, are described which have up to forty-fold greater insect antifeedant activity than salannin itself, and which will facilitate their synthesis and provide for biorational products with a wide spectrum of activity against insect pests.

DETAILED DESCRIPTION OF THE INVENTION

A number of derivatives of salannin were prepared and their structures confirmed by infrared, nuclear magnetic resonance and mass spectroscopy, as well as through chromatographic methods.

Salannin ($C_{34}H_{44}O_9$) is a tetranortriterpenoid which is generally isolated from crude extracts of *A. indica* or *M. dubia* (de Silva et al., 1969, *supra*); Kubo et al. *Tetrahedron* 1986, 42 489–496). by preparative thin-layer chromatography (TLC) (Nakanishi, K. *Recent Adv. Phytochem.* 1975, 9:283–298) or preparative high-performance liquid chromatography (HPLC) (Warthen et al., 1978 *supra*). In nearly all such methods the purity of the preparations are determined by TLC, a technique which we found to be less reliable than analytical HPLC.

We disclose here a method of preparative isolation of salannin of single peak purity, as determined by analytical HPLC using the rapid and inexpensive technique of flash chromatography (Still, W.C., et al., *J. Org. Chem.* 1978, 43, 2923–2925) combined with HPLC, preceded by extraction of salannin from ground neem seeds stirred in n-hexane.

Extraction of salannin from neem seeds was accomplished by the method of Yamasaki et al., *J. Chromatoor.* 1988, 447: 277–283. A suspension of 4.0 kg of ground neem seeds (obtained from India by Vikwood Ltd., Sheboygan, Wis., U.S.A.) in 4.0 L of n-hexane was stirred occasionally at room temperature for several hours. The hexane extract was decanted and the process was repeated with fresh n-hexane five more times. The hexane extracts were pooled and concentrated in vacuo to afford 315 g of a light-brown oil.

Normal-phase analytical TLC was performed on 20×20 cm prescored silica gel GHLF plates (250 μm, Analtech) Reversed-phase analytical TLC was performed on 1×3 inch MKC$_{18}$F plates (200 μm, Whitman). Visualization for analytical TLC was accomplished under shortwave UV light, followed by spraying with a vanillin-sulfuric acid-ethanol (3 g:1.5 mL: 100 mL) spray reagent and heating with a hot air gun.

A 2.0 L flash column (Aldrich) was packed, after removal of fines, with silica gel (60–200 mesh, 15×7.0 cm I.D., J.T. Baker) and equilibrated with n-hexane. The light-brown oil from the hexane extract described above was applied in 105 g batches onto the top of the column. The column was flushed at 40 mL/min with 1.0 L of n-hexane, followed by 2.0 L of dichloromethane. Salannin was then eluted from the column with diethyl ether at 40 mL/min into fractions of 20 mL. Fractions containing salannin, as monitored by TLC, were pooled and rotary evaporated in vacuo yielding 8.7 g total (2.9 g per flash chromatography run) of a light-brown amorphous solid. This material was dissolved to a volume of 100 ml in methanol-water (4:1) and applied in 50-ml batches onto the top of a second flash column (2.00 L, Aldrich) packed with octadecylsilyl-silica gel (ODS) (40 μm, 15×7.0 cm I.D., Regis) in methanol-water (4:1). The column was eluted with methanol-water (4:1) at 20 mL/min into fractions of 20 mL. Fractions containing salannin, again monitored by TLC, were pooled and rotary evaporated in vacuo to yield 2.2. g total (1.1 g per flash chromatography run) of a yellow solid.

Preparative HPLC was carried out with a Micromeritics Model 750 Solvent Delivery System equipped with a Negretti and Zambra injector, a Micromeritics Model 787 variable wavelength UV/visible detector, a Hewlett-Packard 3388A integrator/recorder, and a Gilson Model 201 fraction collector. Chromatography was accomplished using either a normal-phase Alltech Associates silica gel (10-μm particle size) stainless-steel column (25×1.0 cm i.d.), protected with an Alltech Associates stainless-steel guard column (5.0×0.46 cm i.d.) packed with Alltech Associates pellicular silica gel, or a reversed-phase Regis Chemical octadecylsilylsilica gel (ODS) (10-μm particle size) stainless-steel column (25×1.0 cm i.d.), protected with an Alltech Associates pellicular ODS. The solvent (vide infra) was eluted at a flow rate of 5.0 mL/min.

Analytical HPLC was performed as described elsewhere (Yamasaki et al., 1988, *supra*). All prepared derivatives of salannin were purified to >99% purity. The yellow solid (2.2. g) from the ODS flash chromatography step described above was dissolved in acetonitrile to a concentration of 0.55 g/mL and the resulting solution, after filtration, was chromatographed in 0.9 mL batches according to a modification of the reversed-phase preparative HPLC method of Yamasaki et al., (*J. Chromatogr.* 1986, 356, 220–226) for the purification of azadirachtin. In this case, the Phenomenex phenyl column (5 μm particle size) was eluted isocratically with acetonitrile-water (7:13) at a flow-rate of 5.0 mL/min. The recovered salannin (377 mg total) was rechromatographed in the same manner to give 210 mg of a white solid.

Derivatives of salannin were purified by silica gel preparative HPLC as described above.

Infrared (IR) spectra of samples prepared as 2% (w/w) KBr pellets were recorded on a Perkin-Elmer Model 710B infrared spectrophotometer. Proton nuclear magnetic resonance ($^1$H-NMR) spectra were recorded on a 200 MHz IBM AC200 spectrometer equipped with a Cryomagnetic System Inc. magnet. All chemical shifts are expressed as parts per million (δ) downfield from tetramethylsilane internal standard. Only the chemical shifts that differ from those the starting material are listed. Electron impact mass spectra (EI-MS) were recorded at 70 eV on a Varian MAT 112S mass spectrometer using an SS100C computer.

The structural formulae of the compounds whose isolation of preparation are recited in the following section are depicted at the end of the specification in the section entitled "APPENDIX".

Salannin (1a) was isolated and purified from neem (*A. indica*) seeds as described above and was identified by spectral comparison (IR, $^1$H-NMR, EI-MS) and co-chromatography (TLC, HPLC) with an authentic sample. All $^1$H-NMR assignments of salannin have been reported elsewhere (Henderson et al., 1968, *supra*; Kubo et al., 1986, *supra*).

3-Deacetylsalannin and 1-Detigloyl-3-deacetylsalannin. Salannin (60 mg. 0.10 mmol) was stirred with sodium methoxide (108 mg, 2.0 mmol) in 3.0 mL of dry methanol at 25° C. under nitrogen for 24 h. The reaction mixture was then poured into 10-ml of saturated aqueous sodium bicarbonate and extracted three times with 10-ml portions of dichloromethane. The dichloromethane layers were combined, washed once with 10 ml of saturated aqueous sodium chloride, and rotary evaporated in vacuo. Chromatography of the residue by silica gel preparative HPLC (solvent = isopropanol-n-hexane, 3:47) gave two products.

The first product is 3-Deacetylsalannin (1b) (15 mg) as white rosette crystals: IR max (cm$^{-1}$) 3420 (free OH), 1730 (s), 1710 (s), 1650 (m), 1500 (w), 870 (m), 735 (m); $^1$H-NMR (CDCl$_3$), δ1.16 (s, 3 H, 29-Me), 2.42 (d, D$_2$O-exchangeable, J =9.2 Hz, 1 H, 3-OH), 2.64 (dd, J = 9.2, 3.5 Hz, 1 H, H-9), 2.73 (d, J = 12.3 Hz, 1 H, H-5), 3.62 (d, J =7.4 Hz, 1 H, H-28β), 3.87 (ddd, J =9.1, 3.0, 3.0 Hz, changes to dd in D$_2$O-exchange experiment, J =3.0, 3.0 Hz, 1 H, H-3), 4.14 (d, J =7.6 Hz, 1 H, H-28 α); EI-MS, m/z 554 (M+, 75%), 539 (M-CH$_3$, 4), 523 (M-OCH$_3$, 4), 471 (M-COC(CH$_3$) = CHCH$_3$, 5),454 (M-HOCOC(CH.) = CHCH, 7), 421 (11), 397 (9), 283 (73), 259 (22), 230 (24), 215 (16), 202 (15), 185 (18) 173 (30), 147 (23), 119 (17), 83 (CH$_3$,CH = C(CH$_3$)CO+, 100), 55 (CH$_3$CH) = C(CH$_3$)+, 69).

The second product is 1-detigloyl-3-deacetylsalannin (1d) (15 mg) as white rosette crystals: IR max (cm$^{-1}$)

3420 (br), 1735 (s), 1500 (w), 870 (m): $^1$H-NMR (CDCl$_3$) 0.90 (s, 3 H, 19-Me), 1.11 (s, 3 H, 29-Me), 2.41 (dd, J =10.7, 6.5 Hz, 1 H, H-9), 2.70 (d, J =12.6 Hz, 1 H, H-5), 3.54 (ddd, J =3.4, 2.8, 2.8 Hz, changes to dd in D$_2$O-exchange experiment, J =2.8, 2.8 Hz, 1 H, H-1), 3.59 (s, 3H, MeOOC), 3.66 (d, J =7.7 Hz, 1 H, H-28$\beta$), 3.83 (ddd, J =9.3, 2.9, 2.9 Hz, changes to dd in D$_2$O-exchange experiment, J =2.9, 2.9 Hz, 1 H, H-3), 4.02 (d, D$_2$O-exchangeable, J =9.3 Hz, 1 H, 3-OH), 4.11 (d, J =7.4 Hz, 1 H, H-28$_\alpha$), 4.26 (d, J =3.4 Hz, 1 H, H-7), 4.56 (d, D$_2$O-exchangeable, J =3.3 HZ, 1 H, 1-OH), 6.13 (m, 1 H, H-22), 7.14 (m, 1 H, H-23); EI-MS, m/z 472 (M+, 100%) 457 (M-CH$_3$, 10), 441 M-OCH$_3$,(3), 421 (6) 399 (M-CH$_2$COOCH$_3$, 20), 378 (10), 283 (52), 271 (22), 259 (27), 230 (26), 215 (22), 202 (32), 185 (26), 173 (33), 147 (43), 119 (20), 95 (30), 81 (23), 55 (23). The spectral data obtained from these two preparations are in agreement with those reported, elsewhere (Henderson et al., 1964, supra; Henderson et al., 1968, supra; Kraus et al., Liebigs Ann Chem., 1981, 181–189; Kubo et al., 1986, supra.)

Salannic acid (1c) was prepared by a modification of the method of de Silva et al. (1969), supra. Salannin (30 mg, 0.050 mmol) was dissolved in 2.0 mL of 0.5 N NaOH in 50% aqueous methanol and incubated at 60° C. for 6 h. The reaction mixture was poured onto 10 mL of 0.5 N HCl and extracted three times with 10-mL portions of diethyl ether. The organic layers were combined, washed once with 10 mL of saturated aqueous sodium chloride, and rotary evaporated in vacuo. Purification of the crude product by silica gel preparative HPLC (solvent = isopropanol-n-hexane acetic acid, 10:90:1) yielded salannic acid (16 mg). The IR spectrum of salannic acid showed the loss of the absorptions at 1710, 1655, and 735 cm$^{-1}$, assigned to the tigloyl group (Henderson et al., 1968; Butterworth, J. H., et al. J. Chem. Soc.. Perkin Trans. I. 1972, 1445–2450; Yamasaki and Klocke, unpublished data), and the appearance of a very broad, intense absorption at 3400 cm$^{-1}$ characteristic of a carboxylic acid (Silverstein et al., Spectrometric Identification of Organic Compounds, 4th ed. Wiley, New York, 1981, pp. 204–208). All of the $^1$H-NMR absorptions of the tigloyl ($\delta$1.81, 1.94, and 6.96), acetyl ($\delta$1.94, and carbomethoxyl ($\delta$3.24) groups had vanished.

2′,3′-Dihydrosalannin (1e). Salannin (25 mg., 0.041 mmol) in 0.5 ml of ethanol was stirred with 13 mg of 5% palladium on alumina at 25° C. under hydrogen (5 atm) for 15 min. The reaction mixture was then filtered and evaporated in vacuo. The residue was chromatographed by silica gel preparative HPLC (solvent = isopropanol-n-hexane, 2:23) to afford 2′,3′-dihydrosalannin (19 mg): IR max (cm$^{-1}$) 1735 (s), 1500 (w), 870 (m); $^1$H-NMR (CDCl$_3$) $\delta$ 0.95 (t, J =7.4 Hz, 1 H, 4′-Me), 0.96 (t, J =7.4 Hz, 2 H, 4′-Me), 1.23 (d, J =6.5 Hz, 2 H, 5′-Me), 1.30 (d, J =6.9 Hz, 1 H, 5′-Me), 1.45–1.70 (m, 2 H, H-3′$_{ab}$), 1.75–1.95 (m, 1 H, H-2′), 2.07 (s, 3 H, 3-Ac), 3.60 (apparent br s, 2 H, H-28$_{a,b}$), 4.87 (dd, J =2.9, 2.9 Hz, 1 H, H-3); EI-MS, m/z 598 (M+, 100%), 583 (M-CH$_3$, 7), 567 (M-OCH$_3$, 2), 513 (M-COCH(CH$_3$) Ch$_2$Ch$_3$, 4), 504 (10), 496 (M-HOCOCH(CH$_3$)CH$_2$CH$_3$, 5), 421 (17), 397 (5), 283 (30), 259 (23), 235 (17), 230 (9), 202 (9), 185 (9) 173 (14), 147 (13 ), 119 (8), 85 (CH$_3$CH$_2$CH(CH$_3$)CO+, 14), 57 CH$_3$CH$_2$CH(CH$_3$)+, 46).

2′,3′,20,21,22,23-Hexahydrosalannin (2a). Salannin (20 mg., 0.033 mmol) in 0.5 ml of ethanol was stirred with 15 mg of 5% palladium on alumina at 24° C. under hydrogen (10 atm) for 3 h. The reaction mixture was then filtered and rotary evaporated in vacuo. The residue was chromatographed by silica gel preparative HPLC (solvent = isopropanol-n-hexane, 1:9) to give 2′,3′,20,21,22,23-Hexahydrosalannin (13 mg): IR max (cm$^{-1}$) 1735 (s); $^1$H-NMR (CDCl$_3$) $\delta$ 0.94 (t, J =7.1 Hz, 1 H, 4′-Me), 0.95 (t, J =7.1 Hz, 2 H, 4′-Me), 1.19 (d, J =6.9 Hz, 2 H, 5′-Me), 1.27 (d, J =7.8 Hz, 1 H, 5′-Me), 1.40–1.70 (m, 2 H, H-3′$_{ab}$), 1.67 (br d, J =1.2 Hz, 2 H, 18-Me), 1.74 (br d, J =1.5 Hz, 1 H, 18-Me), 1.75–1.95 (m, 1 H, H-2′), 1.95–2.65 (m, 11 H, H-2$_{\alpha\beta}$, H-9, H-11$_{a,b}$, H-16 $_{a,b}$, H-17, H-20, H-22$_{a,b}$), 2.07 (s, 3 H, 3-Ac), 2.68 (d, J =12.6 Hz, 1 H, H-5), 3.28–3.95 (m, 4 H, H-21$_{a,b}$, H-23$_{a,b}$), 3.52 (s, 1 H, MeOOC), 3.53 (s, 2 H, MeOOC), 3.59 (apparent s, 2 H, H-28$_{a,b}$), 5.28 (m, 1 H, H-15); EI-MS m/z 602 (M+, 64%), 587 M-CH$_3$, 6), 571 (M-OCH$_3$, 3) 532 (4), 490 (6), 397 (8), 287 (44), 263 (10), 235 (36), 219 (12), 193 (46), 161 (19), 133 (32), 119 (26), 85 (CH$_3$CH$_3$CH(CH$_3$)CO+, 33), 57 (CH$_3$CH$_2$CH(CH$_3$)+, 100).

1-Detigloyl-3-deacetyl-20,21,22,23-tetrahydrosalannin (2b). 2′,3′,20,21,22,23-Hexahydrosalannin (35 mg, 0.057 mmol) was stirred with sodium methoxide (40 mg, 0.74 mmol) in 1.0 mL of dry methanol at 25° C. for 24 h. The reaction mixture was then poured into 10 mL of saturated aqueous sodium bicarbonate and extracted three times with 10-mL portions of dichloromethane. The dichloromethane portions were combined, washed once with 10 ml of saturated aqueous sodium chloride, and rotary evaporated in vacuo. Chromatography of the residue by silica gel preparative HPLC (solvent = isopropanol-n-hexane, 1:9) afforded (18 mg) as white rosette crystals: IR max (cm$^{-1}$) 3420 (br), 1735 (s); $^1$H-NMR (CDCl$_3$) $\delta$ 0.89 (s, 3 H, 19-Me), 1.10 (s, 3 H, 29-Me), 1.40–2.65 (m, 11 H, H-2$_{\alpha\beta}$, H-9, H-11$_{a,b}$, H-16$_{a,b}$, H-17,H-20, H-22$_{a,b}$), 1.75 (br d, J = 1.6 Hz, 2 H 18-Me), 1.82 (br d, J = 1.5 Hz, 1 H, 18-Me), 2.67 (d, J =12.6 Hz, 1 H, H-5), 3.25–3.90 (m, 4 H, H-21$_{a,b}$, H-23$_{a,b}$), 3.50 (unresolved dd, 1H, H-1), 3.70 (s, 3 H, MeOOC), 3.82 (obscured br d, J =8.7 Hz, changes to obscured br s in D$_2$O-exchange experiment, 1 H, H-3), 4.04 (d, D$_2$O-exchangeable, J =8.7 Hz, 1 H, 3-OH), 4.10 (d, J =7.0 Hz, 1 H, H-28$_a$), 4.60 (br s, D$_2$O-exchangeable, 1 H, 1-OH), 5.31 (m, 1 H, H-15); EI-MS, m/z 476 (M+, 100%), 461 (M-CH$_3$, 15), 445 (M-OCH$_3$, 6), 403 (M-CH$_2$COOCH$_3$,4), 385 (5), 345 (6), 287 (42), 271 (20), 235 (17), 219 (10), 206 (10), 193 (29), 162 (20), 147 (16), 135 (28), 133 (28), 119 (31), 107 (28), 105 (28), 91 (26).

3-O-Methyl-3-deacetylsalannin (1f) was prepared by methylating the hydroxyl group of 3-Deacetylsalannin via a modification of the method of Johnstone and Rose (1979). To a solution of 3-Deacetylsalannin (100 mg, 0.18 mmol) and iodomethane (0.2 mL) in 0.5 mL of dimethyl sulfoxide was added, with vigorous stirring, 0.1 g of finely powdered potassium hydroxide. The suspension was stirred vigorously at 25° C. for 40 min, poured into 10 mL of saturated aqueous sodium bicarbonate, and extracted three times with 10 mL portions of dichloromethane. The organic layers were combined, washed successively with 10 mL portions of saturated aqueous sodium thiosulfate, water, and saturated aqueous sodium chloride, and rotary evaporated in vacuo. Chromatography of the residue by silica gel preparative HPLC (solvent = isopropanol-n-hexane, 1:49, v/v), followed by ODS preparative HPLC (solvent = methanol-water, 7:3, v/v) yielded 3-O-Methyl-3-deacetylsalannin (39 mg): IR max (cm$^{-1}$) 1735 (s), 1705 (s), 1650 (w), 1500 (w), 870 (m), 735 (m); $^1$H NMR (CDCl$_3$) $\delta$ 1.90 (ddd, J$_{2\alpha,2\beta}$=16.4, J$_{2\alpha,1}$= J$_{2\alpha,3}$=3.8, 1

H, H-2$_\alpha$), 2.36 (ddd, J$_{2\beta,2\alpha}$=16.5, J$_{2\beta,1}$= J$_{2\beta,3}$=2.6, 1 H, H-2$_\beta$), 2.70 (dd, J$_{9,11b}$=8.5, J$_{9,11a}$=4.3, 1 H, H-9), 2.89 (d, J$_{5,6}$=12.7, 1 H, H-5), 3.13 (s,3H,3-MeO), 3.32 (dd, J$_{3,2\alpha}$= J$_{3,2\beta}$=2.5,1 H, H-3), 3.56 (d, J$_{28b,28a}$=7.1, 1 H, H-28$_b$), 4.76 (dd, J$_{1,2\alpha}$= J$_{1,2\beta}$=2.7, 1 H, H-1); EI-MS, m/z 568 (M+, 100%), 553 (M-CH$_3$, 7), 485 (M-COC(CH$_3$) = CHCH$_3$, 11), 468 (M-HOCOC(CH$_3$) = CHCH$_3$, 11), 421 (11), 397 (15), 283 (55), 267 (15), 259 (19), 230 (13), 173 (12), 147 (11), 83 (CH$_3$CH = C(CH$_3$)CO+, 62) {(CH$_3$CH = C(CH$_3$)+, 49).

1-Detigloyl-3-O-methyl-3-deacetylsalannin (1 g). 3-O-Methyl-3-deacetylsalannin (50 mg, 0.086 mmol) was dissolved in 2.0 mL of 0.5 M sodium hydroxide in 50% aqueous methanol and stirred at 70° C. for 42 h. The reaction mixture was poured into 10 mL of 0.5 N hydrochloric acid and extracted three times with 10 mL portions of dichloromethane. The organic layers were combined, washed once with 10 mL of water, followed by 10 mL of saturated aqueous sodium chloride, and rotary evaporated in vacuo. The residue was shown by IR to be the desired 3-O-methylsalannic acid. The residue, dissolved in 1.0 mL of dimethyl sulfoxide, was added to a mixture of 0.25 mL of 1.0 M aqueous sodium bicarbonate and 0.2 mL of iodomethane and stirred under nitrogen at 25° C. for 20 h. The reaction mixture was poured into 10 mL of saturated aqueous sodium thiosulfate and extracted three times with 10 mL portions of dichloromethane. The organic layers were combined, washed once with 10 mL of water, followed by 10 mL of saturated aqueous sodium chloride, and rotary evaporated in vacuo. Chromatography of the residue by silica gel preparative HPLC (solvent = isopropanol-n-hexane, 3:47, v/v) yielded 1-Detigloyl-3-O-methyl-3-deacetylsalannin (38 mg) as white rosette crystals: IR max (cm$^{-1}$) 3490 (sharp), 1740 (s), 1500 (w), 870 (m); $^1$H NMR (CDCl$_3$) δ 1.99 (ddd, J$_{2\alpha,2\beta}$=15.7, J$_{2\alpha,1}$= J$_{2\alpha,3}$=2.8, 1 H, H-2$_\alpha$), 2.18 (ddd, J$_{2\beta,2\alpha}$=14.8, J$_{2\beta,1}$= J$_{2\beta,3}$=3.0, 1 H, H-2$_\beta$), 2.26 (dd, J$_{11a,11b}$=14.2, J$_{11a,9}$=5.9, 1 H, H11$_a$), 2.38 (dd, J$_{11b,11a}$=14.2, J$_{11b,9}$=6.3, 1 H, H-11$_b$), 2.58 (d, J$_{5,6}$=12.6, 1 H, H-5), 2.70 (dd, J$_{9,11a}$= J$_{9,11b}$=6.1 1 H, H-9), 3.37 s, 3 H, 3-MeO), 3.41 (dd, J$_{3,2\alpha}$= J$_{3,2\beta}$=2.7, 1 H, H-3), 3.48 (s, 3 H, MeOOC), 3.51 (ddd, J$_{1,OH}$=9.6, J$_{1,2\alpha}$= J$_{1,2\beta}$=2.9, changes to dd in D$_2$O-exchange experiment, J$_{1,2\alpha}$=J$_{1,2\beta}$=2.9, 1 H, H-1), 3.66 (d, D$_2$O-exchangeable, J$_{OH,1}$=9.6, 1 H, 1-OH), 3.96 (br d, J$_{28a,28b}$=7.0, J$_{28a,29}$<1.0, 1 H, H-28a), 5.52 ddq, J$_{15,16a}$= J$_{15,16b}$=7.0, J$_{15,18}$=1.8, 1 H, H-15), 6.34–6.38 (m, 1 H, H-22); EI-MS, m/z 486 (M+, 100%), 471 (M-CH$_3$, 4), 283 (11), 259 (6), 230 (5), 202 (9), 173 (7), 147 (7), 59 (11), 55 (9).

1,3-O,O-Dimethyl-1-detigloyl-3-deacetylsalannin (1h). To a solution of 1-Detigloyl-3-deacetylsalannin (60 mg, 0.13 mmol) and iodomethane (0.2 mL) in 0.5 mL of dimethyl sulfoxide was added, with vigorous stirring, 0.1 g of finely powdered potassium hydroxide. The suspension was stirred vigorously at 25° C. for 60 min, poured into 10 mL of saturated aqueous sodium bicarbonate, and extracted three times with 10 mL portions of dichloromethane. The organic layers were combined, washed successively with 10 mL portions of saturated aqueous sodium thiosulfate, water, and saturated aqueous sodium chloride, and rotary evaporated in vacuo. Purification of the crude product by silica gel preparative HPLC (solvent = isopropanol-D-hexane, 1:24, v/v) yielded 1h (40 mg): IR max (cm$^{-1}$) 1735 (s), 1500 (w), 870 (m); $^1$H NMR (CDCl$_3$) δ1.73 (ddd, J$_{2\alpha,2\beta}$=16.4, J$_{2\alpha,3}$=3.1, 1H, H-2$_\alpha$), 2.36 (ddd, J$_{2\beta,2\alpha}$=16.2, J$_{2\beta,1}$= J$_{2\beta,3}$=2.6, 1 H, H-2$_\beta$), 2.64 (d, J$_{5,6}$=12.7, 1 H,H-5), 2.88 (dd, J$_{9,11a}$= J$_{9,11b}$=6.0, 1 H,H-9), 3.02 (dd, J$_{1,2\alpha}$= J$_{1,2\beta}$=2.6, 1 H, H-1), 3.27 (dd, J$_{3,2\alpha}$= J$_{3,2\beta}$=2.6, H, H-3), 3.29 (s, 3 H, 1-MeO), 3.32 (s, 3 H,3-MeO), 3.43 (s, 3H,MeOOC), 4.01 (br d, J$_{28a,28b}$=7.5, J$_{28a,29}$<1.0, 1 H, H-28$_a$), 4.16 (d, J$_{7,6}$=3.3, 1 H, H-7), 5.56 (ddq, J$_{15,16a}$= J$_{15,16b}$=7.0, J$_{15,18}$=1.5, 1 H, H-15), 6.31–6.34 (m, 1 H,H-22), 7.24–7.28 (m, 1 H, H-23); EI-MS, m/z 500 (M+, 100%), 485 (M-CH$_3$, 7),420 (7), 406(13),397 (16), 283 (63), 259 (20), 101 (21), 85 (26), 55 (20).

1-o-Acetyl-1-detigloylsalannin (1i). This diacetate was prepared by a modification of the method of Henderson et al. (1968). Salannic acid (96 mg, 0.21 mmol) and acetic anhydride (195 μL, 2.1 mmol) were dissolved together in 0.8 mL of drypyridine and heated at 70° C. under nitrogen for 20 h. The reaction mixture was poured into 20 mL of 0.5 N hydrochloric acid and extracted three times with 20-mL portions of dichloromethane. The organic layers were combined, washed once with 20 mL of saturated aqueous sodium bicarbonate, followed by 20 mL of saturated aqueous chloride, and rotary evaporated in vacuo. Chromatography of the residue by silica gel preparative HPLC (solvent = isopropanol-n-hexane, 1:24, v/v), followed by ODS preparative HPLC (solvent = methanol-water, 7:3, v/v) gave 1i (70 mg) as white needles: IR max (cm$^{-1}$), 1735 (s), 1500 (w), 870 (m); $^1$H NMR (CDCl$_3$) δ1.20 (br s, J$_{29,28a}$<1.0, 3 H, 29-Me), 1.65 (d, J$_{18,15}$=1.4, 3 H, 18-Me), 2.07 (s, 3 H, Ac), 2.14 (s, 3 H, Ac), 2.73 (dd, J$_{9,11b}$=8.8, J$_{9,11a}$=3.3, 1 H, H-9), 3.31 (s, 3 H MeOOC). 3.71 (br d, J$_{28a,28b}$=7.6, J$_{28a,29}$<1.0, 1 H, H-28$_a$), 4.17 (d, J$_{3,2\alpha}$=J$_{3,2\beta}$=2.9, 1 H, H-3), 4.94 dd, J$_{1,2\alpha}$= J$_{1,2\beta}$=2.9, 1 H, H-1), 6.32-6.35 (m, 1 H, H-22), 7.26–7.30 (m, 1 H, H-23); EI-MS, m/z 556 (M+, 100%), 541 (M-CH$_3$, 5), 421 (13), 283 (4), 259 (6), 235 (5), 100 (7).

3-o-Methyl-3-deacetyl-2',3',20,21,22,23-hexahydrosalannin (2c). 3-O-Methyl-3-deacetylsalannin (40 mg, 0.069 mmol) in 0.5 mL of ethanol was stirred with 30 mg of 5% palladium on alumina at 24° C. under hydrogen (10 atm) for 2 h. The reaction mixture was then filtered and rotary evaporated in vacuo. The residue was chromatographed by silica gel preparative HPLC (solvent = isopropanol-n-hexane, 1:19, v/v), followed by ODS preparative HPLC (solvent = methanol-water, 7:3, v/v) to obtain 2c (23 mg): IR max (cm$^{-1}$) 1735 (s), 1725 (s); $^1$H NMR )(CDC$_3$) δ0.94 (t, J$_{4',3'}$=7.6, 1 H, 4'-Me), 0.95 (t, J$_{4',3'}$=7.4, 2 H, 4'-Me), 1.16 (d, J$_{5',2'}$=7.0, 2 H, 5'-Me), 1.24 (d, J$_{5',2'}$=7.1, 1 H, 5'-Me), ca. 1.4–1.7 (m, 2 H, H-3'$_a$, H-20), 1.66 (d, J$_{18,15}$=1.3, 2H, 18-Me), ca. 1.4–1.7 (m, 2 H, H-3'$_a$, H-20), 1.66 (d, J$_{18,15}$=1.3, 2 H, 18-Me), ca. 1.7–2.0 (m, 1 H, H-3'$_b$), 1.73 (d, J$_{18,15}$=1.4, 1 H, 18-Me), ca. 1.8–2.3 (m, 2 H, H-22$_{a,b}$), ca. 2.3–2.6 (m, 1 H, H-2'), ca. 2.4–2.6 (m, 1 H, H-17), 2.62 (dd, J$_{9,11b}$=9.5, J$_{9,11a}$=3.4, 1 H, H-9), 2.77 (d, J$_{5,6}$=12.6, 1 H,H-5), 3.20 (s, 3 H, 3-MeO), 3.26 (dd, J$_{3,2\alpha}$= J$_{3,2\beta}$=3.0, 1 H, H-3), 3.31 (dd, J$_{21a,20}$= J$_{21a,21b}$=8.6, 0.33 H, H-21$_a$), 3.37 (dd, J$_{21a,20}$= J$_{21a,21b}$=8.5, 0.67 H, H-21$_a$), 3.51, (s, 1 H, MeOOC), 3.52 (s, 2 H, MeOOC), 3.60–3.95 (m, 3 H, H-21$_b$,H-23$_{a,b}$), 4.06 (br d, J$_{28a,28b}$=7.6, J$_{28a,29}$<1.0, 1 H, H-28$_a$), 4.09 (d, J$_{7,6}$=3.3, 1 H, H-7), 4.70 (dd, J$_{1,2\alpha}$= J$_{1,2\beta}$=3.0, 1 H, H-1), 5.26 (ddq, J$_{15,16a}$= J$_{15,16b}$=7.0, J$_{5,18}$ =1.4, 0.33 H, H-15), 5.29 (ddq, J$_{15,16a}$= J$_{15,16b}$=7.0, J$_{15,18}$=1.3, 0.67 H, H-15); EI-MS, mz 574 (M+, 100%),559 (M-CH$_3$, 13), 287 (37), 267 (16), 234 (12), 193

(27), 133 (11), 119 (11), 85 ($CH_3CH_2CH(CH_3)CO+$, 20), 57 ($CH_3CH_2CH(CH_3)^+$, 48).

1-Detigloyl-3-o-methyl-3-deacetyl-20,21,22,23-tetrahydrosalannin (2d). 3-O-methyl-3-deacetyl-2',3',20,21,22,23-hexahydrosalannin (50 mg, 0.085 mmol) was dissolved in 2.0 mL of 0.5 M sodium hydroxide in 50% aqueous methanol and stirred at 70° C. for 42 h. The reaction mixture was poured into 10 mL of 0.5 N hydrochloric acid and extracted three times with 10mL portions of dichloromethane. The organic layers were combined, washed once with 10 mL of water, followed by 10 mL of saturated aqueous sodium chloride, and rotary evaporated in vacuo. The residue was shown to be, by IR, the desired 3-o-methyl-20,21,22,23-tetrahydrosalannic acid. The residue, dissolved in 1.0 mL of dimethyl sulfoxide, was added to a mixture of 0.25 mL of 1.0 M aqueous sodium bicarbonate and 0.2 mL of iodomethane and stirred under nitrogen at 25° C. for 20 h. The reaction mixture was poured into 10 mL of saturated aqueous sodium thiosulfate and extracted three times with 10-mL portions of dichloromethane. The organic layers were combined, washed once with 10 mL of water, followed by 10 mL of saturated aqueous sodium chloride, and rotary evaporated in vacuo. The crude product was purified by silica gel preparative HPLC (solvent = isopropanol-n-hexane, 3:17, v/v) to give 2d (32 mg): IR max (cm$^{-1}$) 3510 (br), 1735 (s); $^1$H NMR (CDCl$_3$) δ1.97 (ddd, $J_{2α,β}=15.9$, $J_{2α,1}=J_{2α,3}=3.7$, 1 H, H-2 $_α$), 2.18 (ddd, $J_{2β,2α}=15.5$, $J_{2β,1}=J_{2β,3}=3.0$, 1 H, H-2β), 2.55 (d, $J_{5,6}=12.2$, 1 H, H-5), 2.72 (dd, $J_{9,11a}=J_{9,11b}=6.0$, 1 H, H-9), 3.37 (s, 3 H, 3-MeO), 3.41 (dd, $J_{3,2α}=J_{3,2β}=2.8$, 1 H, H-3), 3.48 (ddd, $J_{1,OH}=9.7$, $J_{1,2α}=J_{1,2β}=3.0$, changes to dd in D$_2$O-exchange experiment ,$J_{1,2α}=J_{1,2β}=3.0$, 1 H, H-1), 3.60 (s, 3 H, MeOOC), 3.63 (d, D$_2$O-exchangeable, $J_{OH,1}=9.7$ 1 H, 1-OH), 3.94 (br d, $J_{28a,28b}=7.1$, $J_{28a,29}<1.0$, 1 H, H-28$_a$), 5.36 (ddq, $J_{15,16a}=J_{15,16b}=7.0$, $J1215,18=1.6$,0.33 H, H-15), 5.40 (ddq, $J_{15,16a}=J_{15,16b}=7.0$, $J_{15,18}=1.6$, 0.67 H-15); EI-MS, m/z 490 (M+, 100%), 475 (M-CH$_3$, 4), 403 (11), 287 (16), 1093 (16), 107 (11), 91 (14), 85 (11), 81 (11),59 (13), 55 (19).

1, 3-O-O-Dimethyl-1-detigloyl-3-deacetyl-20,21,22,23-tetrahydrosalannin (2e). 1,3-O-O-Dimethyl-1 -detigloyl-3-deacetylsalannin (30 mg, 0.060 mmol) in 0.5 mL of ethanol was stirred with 25 mg of 5% palladium on alumina at 25° C. under hydrogen (10 atm) for 2 h. The reaction mixture was then filtered and rotary evaporated in vacuo. The residue was chromatographed by silica gel preparative HPLC (solvent = isopropanol-n-hexane, 1:9,v/v) to afford 2e (26 mg): IR max (cm$^{-1}$) 1735 (s); $^1$H NMR (CDCl$_3$) δca. 1.4–1.8 (m, 1 H, H-20), 1.70 (d, $J_{18,15}=1.5$, 2 H, 18-Me),1.77 (d, $J_{18,15}=1.8$, 1 H, 18-Me), ca. 1.8–2.4 (m, 8 H, H-2$_{α,β}$, H-11$_{a,b}$, H-16$_{a,b}$, H-22$_{a,b}$), ca. 2.5–2.6 (m, 1 H, H-17), 2.79 (dd, $J_{9,11a}=J_{9,11b}=6.2$, 0.33 H, H-9), 2.81 (dd, $J_{9,11a}=J_{9,11b}=6.2$, 0.67 H, H-9), 2.96 (dd, $J_{1,2α}=J_{1,2β}=3.0$, 0.33 H,H-1), 3.00 (dd, $J_{1,2α}=J_{1,2β}=3.0$, 0.67 H, H-1),3.26 (s, 1 H, 1-MeO), 3.27 (s,2 H, 1-MeO), 3.34 (dd, $J_{21a,20}=J_{21a,21b}=8.5$, 0.33 H, H-21$_a$), 2.39 (dd, $J_{21a,20}=J_{21a,21b}=8.5$, 0.67 H, H-21$_a$), 3.45–3.95 (m, 3 H, H-21$_b$, H-23$_{a,b}$), 3.58 (s, 2 H, MeOOC), 3.59 (s, 1 H,MeOOC), 5.35–5.48 (m, 1 H, H-15); EI-MS, m/z 504 (M+, 100%),489 (M-CH$_3$, 11) 403 (48), 287 (61), 235 (13), 193 (18), 119.(11), 101 (28), 85 (24),59 (11),55 (15).

3-Deacetoxy-2',3',20,21,22,23-hexahydrosalannin (2f). 3-Deacetylsalannin (100 mg, 0.18 mmol) was stirred with methanesulfonyl chloride (70 μL, 0.90 mmol) in 0.4 mL of pyridine at 25° C. for 3 h. The reaction mixture was poured into 10 mL of 0.5 N hydrochloric acid and extracted three times with 10 mL portions of dichloromethane. The organic layers were combined, washed once with 10 mL of 0.5 N hydrochloric acid, followed by 10 mL of saturated aqueous sodium chloride, and rotary evaporated in vacuo. The residue, shown by IR to contain no remaining hydroxyl, was dissolved in 1.0 mL of dimethyl sulfoxide and then, 0.31 g (0.54 mmol) of tetra-n-butylammonium oxalate disalt (Corey and Terashima, Tetrahedron Lett. 1972, 111–113) was added. The reaction mixture was heated at 70° C. for 16 h before pouring into 20 mL of saturated aqueous sodium bicarbonate and extracting three times with 20 mL portions of dichloromethane. The organic layers were combined, washed once with 20 mL of water, followed by 20 mL of saturated aqueous sodium chloride, and rotary evaporated in vacuo. The residue, following chromatography by silica gel preparative HPLC (solvent = isopropanol-n-hexane, 3:97, v/v), was stirred with 20 mg of 5% palladium on alumina in 0.5 mL of ethanol at 25° C. under 10 atm of hydrogen for 3 h. The reaction mixture wa filtered and rotary evaporated in vacuo. The residue was chromatographed by silica gel preparative HPLC (solvent = isopropanol-n-hexane, 1:19, v/v) to yield 2f (24 mg): IR max (cm$^{-1}$) 1739 (s); $^1$H NMR (CDCl$_3$) δ0.94 (t, $J_{4',3'}=7.4$, 1 H, 4'-Me), 0.95, (t, $J_{4',3'}=7.4$, 2 H, 4'-Me), 1.16 (d, $J_{5',2'}=6.9$, 2 H, 5'-Me), 1.25 (d, $J_{5',2'}=7.3$, 1 H, 5'- Me), ca. 1.4–2.6 (m, 16 H, H-2$_{,αβ}$, H-2', H-3$_{α,β}$, H-3'$_{a,b}$, H-9, H-11$_{a,b}$, H-16$_{a,b}$, H-17, H-20, H-22$_{a,b}$), 1.66 (apparent br s, $J_{18,15}<1.0$, 2 H, 18-Me), 1.73 (d, $J_{18,15}=1.6$, 1 H, 18-Me), 2.27 (d, $J_{5,6}=12.3$, 1 H, H-5), 3.31 (dd, $J_{21a,20}=J_{21a,21b}=8.6$, 0.33 H, H-21$_a$), 3.37 (dd, $J_{21a,20}=J_{21a,21b}=8.3$, 0.67 H, H-21$_a$), 3.51 (s, 1 H, MeOOC), 3.53 (s, 2 H, MeOOC), 3.54 (br d, $J_{28a,28b}=7.3$, $J_{28a,29}<1.0$, 1 H, H-28$_a$), 3.60–3.95 (m, 3 H, H-21$_b$, H-23$_{a,b}$), 3.69 (d, $J_{28b,28a}=7.2,1$ H, H-28$_b$), 3.91 (dd, $J_{6,5}=12.6$, $J_{6,7}=3.3$, 1 H, H-6), 4.08 (d, $J_{7,6}=3.3$, 0.33 H, H-7) 4.09 (d, $J_{7,6}=3.3$, 0.67 H, H-7).

Fourteen derivatives of salannin (1a) were prepared and their structures were confirmed by IR, $^1$H NMR, and EI-MS. 3-Deacetylsalannin (1b) was purified from neem seeds as described by Yamasaki et al. (1988), supra. Alternatively 1b could be obtained, albeit at somewhat low (25%) yields, through transesterification of 1a with sodium methoxide, a reaction which yielded equal amounts of 1-detigloyl-3-deacetylsalannin (1d).

Saponification of 1a with aqueous methanolic sodium hydroxide yielded salannic acid (1c). The IR spectrum of salannic acid showed the loss of the bands at 1710, 1655, and 735 cm$^{-1}$, assigned to the tigloyl group (Henderson et al., 1968 supra; Butterworth et al., 1972 supra; Yamasaki and Klocke, J. Agric. Food Chem. 1987, 35:467–471), and the appearance of a very broad, intense absorption at 3400 cm$^{-1}$ characteristic of a carboxylic acid (Silverstein et al., supra). All of the $^1$H NMR signals of the tigloyl (δ3.24) groups had vanished EI-MS showed a parent ion at m/z 458 as reported by de Silva et al., supra.

Although 1-detigloyl-3-deacetylsalannin (1d) could be prepared by transesterification of 1a with sodium methoxide, we could obtain better yields (81% compared to 25%) of 1d by methylating the sodium salt of the carboxylic acid group of 1c with iodomethane in dimethyl sulfoxide. The very broad, intense absorption at 3400 cm$^{-1}$ (carboxylic acid and two hydroxyl groups) in the IR spectrum of 1c became a less broad and less intense band in 1d. In addition, the carbonyl stretching band at 1700 cm$^{-1}$ of 1c changed to 1735 cm$^{-1}$ in the IR spectrum of 1d, indicating the conversion of the carboxylic acid to the methyl ester. $^1$H NMR showed the presence of a carbomethoxyl group (singlet at δ3.59) in 1d as well as two D$_2$O-exchangeable hydroxyl groups at positions 1 and 3.

2′,3′-Dihydrosalannin (1e) was made by hydrogenation of salannin over palladium on alumina. The IR bands of the tigloyl group at 1710, 1655, and 735 cm$^{-1}$ had disappeared. In the $^1$H NMR spectrum, the 4′-methyl (δ1.82), 5′-methyl (δ1.92–1.96), and 3′-vinyl (δ6.96) signals of 1a were replaced in 1e by two overlapping triplets (δ0.95 and 0.96, 1:2 ratio), two overlapping doublets (δ1.23 and 1.30, 2:1 ratio), and an unresolved multiplet (δ1.4–2.0), respectively. Another multiplet (δ2.3–2.6) was seen for the proton at the 2′ position. The two sets of doublet and triplet signals observed for the 5′- and 4′-protons, respectively, most likely reflect the fact that a new chiral center at position 2′ had been created (Silverstein et al., *supra* at p. 207–209; Yamasaki and Klocke, *supra*). The two diastereomers appear to have been produced in a 2:1 ratio, although the favored configuration at 2′ is unknown.

Methylation of the hydroxyl group of 1b afforded 3-O-methyl-3-deacetylsalannin (1f). Absence of a free hydroxyl group in 1f was indicated by the disappearance of the hydroxyl band at 3420 cm$^{-1}$ in the IR spectrum and the hydroxyl signal at δ2.42 in the $^1$H NMR spectrum of 1b. In the $^1$H NMR spectrum of 1f, a new singlet appeared at δ3.13, consistent with a methoxyl group.

1-Detigloyl-3-O-methyl-3-deacetylsalannin (1g) was made by first saponifying the tiglate and methyl esters of 1f and then, remethylating the carboxylic acid group according to a modification of the method of Mehta (*Synthesis* 1972, p. 262). The IR spectrum of 1g contained a hydroxyl band at 3490 cm$^{-1}$, but lacked the bands of the tigloyl group at 1705, 1650, and 735 cm$^{-1}$. The $^1$H NMR spectrum of 1g contained a D$_2$O-exchangeable proton signal at δ3.66 and lacked the signals of the tigloyl group.

Methylation of the two hydroxyl groups of 1d in a manner similar to the preparation of 1f yielded 1,3-O,O-dimethyl-1-detigloyl-3-deacetylsalannin (1h). The IR band at 3420 cm$^{-1}$ and the two D$_2$O-exchangeable $^1$H NMR signals (δ4.02 and 4.56) seen with 1d were absent in the corresponding spectra of 1h. Singlets were observed (δ3.29 and 3.32) in the $^1$H NMR spectrum of 1h for the methoxyl groups at positions 1 and 3, respectively.

The hydroxyl groups of 1d were acetylated according to a modification of the method of Henderson et al. (1968), *supra*, to afford the known 1-O-acetyl-1-detigloylsalannin (1i). The $^1$H NMR spectrum of 1i was in agreement with those reported by Henderson et al. (1964, 1968), *supra*, and de Silva et al., *supra*.

When 1a was hydrogenated over a palladium catalyst at higher pressure (10 vs. 5 atm) and for a longer reaction time (360 vs. 15 min) than that used to make 1e, the furan ring was reduced as well as the tigloyl group. The IR spectrum of 2′, 3′,20,21,22,23-hexahydrosalannin (2a) showed the loss of the furan moiety bands at 1500 and 870 cm$^{-1}$. In addition to the changes in the $^1$H NMR spectrum observed with 1e, the signals of the furan ring protons at positions 21, 22, and 23 (δ7.31–7.35, 6.28–6.31, and 7.24–7.28, respectively) in 1a were replaced by two doublet-of-doublets at δ3.32 and 3.38 (1:2 ratio, respectively, proton 21$_{a,b}$) and 1.80–2.35 (protons 22$_{a,b}$) in 2a. A new multiplet at δ1.4–2.0 (proton at position 20) was also observed. The doublet (J$_{18,15}$=1.3) at δ1.67 of the 18-methyl group and the singlet at δ3.24 of the carbomethoxyl group of 1a were replaced in 2a by two doublets at δ1.67 and 1.74 (2:1 ratio, J$_{18,15}$=1.2 and 1.5, respectively) of the 18-methyl group and two singlets at δ3.52 and 3.53 (1:2 ratio) of the carbomethoxyl group. The signal for the proton at position 17 had also changed from a broadened doublet (δ3.63) to a multiplet within the envelope at δ2.30–2.65. The two sets of signals observed for each of the 18-methyl and carbomethoxyl protons (as well as for protons 7, 15, and 21$_a$) is probably a consequence of the hydrogenation at either face of the prochiral carbon at position 20. Similar to our result with the hydrogenation of the tigloyl group, one face was preferentially reduced by a 2:1 ratio.

Transesterification of 2a with sodium methoxide afforded 1-detigloyl-3-deacetyl-20,21,22,23-tetrahydrosalannin (2b). The IR spectrum of 2b showed the loss of the tigloyl and furan ring bands and the presence of new hydroxyl bands at 3420 cm$^{-1}$. $^1$H NMR showed two D$_2$O-exchangeable protons, the loss of the acetyl and tigloyl signals, and the same changes in the furan ring signals as those seen with 2a. In this case, partitioning of the carbomethoxyl signal (δ3.70) into two sets was not observed.

Hydrogenation of 1f and 1h over a palladium catalyst gave 3-O-Methyl-3-deacetyl-2′,3′,20,21,22,23-hexahydrosalannin (2c) and 1,3-O,O-dimethyl-1-detigloyl-3-deacetyl-20,21,22,23-tetrahydrosalannin (2e), respectively. The appropriate spectral changes observed in the hydrogenation of 1a to give 2a were likewise observed in the hydrogenation of 1f and 1h to give 2c and 2e, respectively.

1-Detigloyl-3-O-methyl-3-deacetyl-20,21,22,23-tetrahydrosalannin (2d) was prepared from 2c in a manner analogous to the preparation of 1g from 1f. The IR spectrum of 2d showed a hydroxyl band at 3510 cm$^{-1}$ and lacked the carbonyl stretching band at 1725 cm$^{-1}$ (α-methylbutyrate ester). $^1$H NMR showed the presence of a D$_2$O-exchangeable proton (δ3.63) and the absence of all of the δ-methylbutyryl group protons.

3-Deacetoxy-2′,3′,20,21,22,23-hexahydrosalannin (2f) was smoothly prepared from 1b in three steps. The hydroxyl group of 1b was first mesylated and then eliminated in an E2 process using a modification of the method of Corey and Terashima, *supra*. The resulting olefin, as well as the furan ring and tiglate carbon-carbon double bonds, were subsequently hydrogenated over palladium.

In the $^1$H NMR spectra of 1a and nearly all of the derivatives reported in this study (two exceptions will be discussed below), broadening (J$_{28a,29}$= J$_{29,28}$<1.0) of the signal was observed for protons 28$_a$ (doublet) and 29-methyl (singlet). This example of the "W-conformation" long range coupling (Silverstein et al., *supra* at p. 207–209) was reported previously for 1i (Henderson et al., 1964, 1968, *supra*) and helped distinguish proton 28$_a$ from 28$_b$. In two of the derivatives in the present study (1e and 2a), this broadening effect was not observed since the $^1$H NMR signals of protons 28$_a$ and 28$_b$, normally doublets due to geminal coupling, coalesced into an apparent singlet. These two derivatives represent examples of structures containing chemically and magnetically nonequivalent (diastereotopic) coupled protons that have fortuitously identical chemical shift values.

In every case, the molecular ion was observed in the EI-MS. A major peak was also seen at m/z 283 in 1a and all of its derivatives whose furan ring was not reduced. The identity of this fragment is unknown. However, it probably includes the furan ring moiety since the six derivatives, whose furan ring was completely hydrogenated (series 2a-2f), showed a major peak at m/z 287 instead of 283.

The antifeedant activity of salannin (1a) and fourteen of its derivatives against third-instar *L. decemlineata* is shown in Table 1. The chemical structures of these compounds are shown in Formulae I and II. Modifications of four chemical points of the parent salannin molecule resulted in changes in the antifeedant activity. Table 1 shows the antifeedant activity of salannin, each of the 14 derivatives, azadirachtin, and kelthane against Colorado potato beetle (*Leptinotarsa decemlineata* (Say)) larvae using a leaf disk "choice" bioassay. $PC_{95}$ is the minimal protective concentration at which >95% of the control disks were eaten, while <5% of the treated disks were eaten in choice bioassays. $PC_{50}$ is the minimal protective concentration at which >50% of the control disks were eaten, while <5% of the treated disks were eaten in choice bioassays.

TABLE 1

| Test Compound | $PC_{95}$ $(\mu g)^a$ | $PC_{50}$ $(\mu g)^b$ |
|---|---|---|
| Salannin (1a) | >400 | 150 |
| 3-Deacetylsalannin (1b) | >400 | 25 |
| 1-Detigloyl-3-deacetylsalannin (1d) | >400 | 25 |
| 1-Detigloyl-3-O-methyl-3-deacetylsalannin (1g) | >400 | 400 |
| 1-O-Acetyl-1-detigloylsalannin (1i) | >400 | >400 |
| 2',3'-Dihydrosalannin (1e) | 200 | — |
| 3-O-Methyl-3-deacetylsalannin (1f) | 100 | — |
| 1,3-O,O-Dimethyl-1-detigloyl-3-deacetyl-20,21,22,23-tetrahydrosalannin (2e) | 100 | — |
| Salannic Acid (1c) | 50 | — |
| 1,3-O,O-Dimethyl-1-detigloyl-3-deacetylsalannin (1h) | 50 | — |
| 1-Detigloyl-3-deacetyl-20,21,22,23-tetrahydrosalannin (2b) | 50 | — |
| 1-Detigloyl-3-O-methyl-3-deacetyl-20,21,22,23-tetrahydrosalannin (2d) | 50 | — |
| 2',3',20,21,22,23-Hexahydrosalannin (2a) | 25 | 10 |
| 3-O-Methyl-3-deacetyl-2',3',20,21,22,23-hexahydrosalannin (2c) | 10 | 2 |
| 3-Deacetoxy-2',3',20,21,22,23-hexahydrosalannin (2f) | 10 | — |
| Azadirachtin | 75 | 19 |
| Kelthane | 6 | 2 |

First, hydrogenation of the furan ring to the tetrahydrofuran ring increased the antifeedant activity. For example, the activity of 1d ($PC_{95}>400$ $\mu g$), a diol of 1a, was increased more than eightfold via hydrogenation to the diol of tetrahydrosalannin (2b, $PC_{95}=50$ $\mu g$). In addition, the activity of 1e ($PC_{95}=200$ $\mu g$), hydrogenated only at the tigloyl moiety, was increased eightfold via hydrogenation of its furan ring to yield 2a ($PC_{95}=25$ $\mu g$).

Second, replacement of the acetoxyl group at position 3 by a methoxyl group increased the antifeedant activity. For example, the activity of 1a ($PC_{95}>400$ $\mu g$) increased via derivatization to 1f ($PC_{95}=100$ $\mu g$) as did that of 2a ($PC_{95}=25$ $\mu g$) via derivatization to 2c ($PC_{95}=10$ $\mu g$). A similar increase in antifeedant activity was observed when the acetoxyl group at position 3 was replaced by hydrogen (2f, $PC_{95}=10$ $\mu g$).

Third, modifications of the tigloyl group resulted in some changes in antifeedant activity. Hydrogenation of the tigloyl moiety of 1a ($PC_{95}>400$ $\mu g$) to give the α-methylbutyryl group of 1e ($PC_{95}=200$ $\mu g$) resulted in at least a twofold increase in the activity. In general, deesterification of the tigloyl or the α-methylbutyryl groups resulted in a reduction of activity. Examples include 2c ($PC_{95}>10$ $\mu g$), which was fivefold more active than 2d ($PC_{95}=50$ $\mu g$), and 1f ($PC_{95}=100$ $\mu g$), which was more than fourfold more active than 1g ($PC_{95}>400$ $\mu g$). O-Methylation at position 1 of the detigloyl derivatives had opposite effects on the activity depending on whether the derivatives contained a furan or a tetrahydrofuran ring. For example, 1h ($PC_{95}=50$ $\mu g$), with a methoxyl group at position 1 and a furan ring at position 17, was found to be more than eightfold more active than 1g ($PC_{95}>400$ $\mu g$), which contained a hydroxyl group at position 1 instead of the methoxyl group. On the other hand, 2d ($PC_{95}=50$ $\mu g$), with a hydroxyl group at position 1 and a tetrahydrofuran ring at position 17, was twice as potent as 2e ($PC_{95}=100$ $\mu g$), which contained a methoxyl group at position 1 instead of the hydroxyl group.

Fourth, saponification of the methyl ester at position 11 increased the antifeedant activity. For example, salannic acid (1c, ($PC_{95}=50$ $\mu g$) was at least eight-fold more active than the 1,3-diol, 1d ($PC_{95}>400$ $\mu g$).

Salannin (1a) and four of its nonhydrogenated derivatives (1b, 1d, 1g, and 1i) did not exhibit 95% protection (i.e., $PC_{95}$ values) at 400 $\mu g$/disk, the highest concentration tested. However, some antifeedant activity was observed at 400 $\mu g$/disk such that $PC_{50}$ values, the protective concentration at which >50% of the control disks were eaten, while 22 5% of the test disks were eaten, were determined for these compounds (Table 1). For comparative purposes, the $PC_{50}$ values were also determined for two of the most active of the salannin derivatives (2c, $PC_{50}=2$; 2a, $PC_{50}=10$ $\mu g$), azadirachtin ($PC_{50}=19$ $\mu g$) and kelthane ($PC_{50}=2$ $\mu g$) (Table 1). The $PC_{50}$ values for these compounds were 2- to 5-fold lower than their respective $PC_{95}$ values.

Replacement of the tigloyl moiety of salannin (1a, $PC_{50}=150$ $\mu g$) to form the 1,3-diacetate (1i, $PC_{50}>400$ $\mu g$) resulted in a loss of the antifeedant activity. More active was the 1,3-diol (1d, $PC_{50}=25$ $\mu g$). Its activity was unaffected by the presence of a tigloyl group esterified at position 1 (1b, $PC_{50}=25$ $\mu g$). However, methylation of its C-3 hydroxyl group to form 1g ($PC_{50}=400$ $\mu g$) resulted in a 16-fold reduction in the antifeedant activity.

These data indicate that the potency of salannin as an antifeedant against third-instar *L. decemlineata* larvae is increased by over 40-fold by a combination of hydrogenation of the furan ring and the tigloyl group and by replacement of the acetoxyl group by a methoxyl group or a hydrogen atom. The two derivatives prepared in this manner (2c and 2f) were found to be 7.5-fold more active as antifeedants against *L. decemlineata* than the natural plant compound, azadirachtin ($PC_{95}=75$ $\mu g$), and they were about as active as the commercial miticide, kelthane ($PC_{95}=6$ $\mu g$) (Table 1).

Azadirachtin is currently being investigated as a source of and model compound for a new commercial insect antifeedant (Klocke, in *Economic and Medicinal Plant Research;* Wagner et al., Eds.; Academic; London 1989; Vol. 3, p. 103–144). Kelthane has been reported as an antifeedant against the Colorado potato beetle in laboratory and field studies (Walgenbach and Wyman, *J. Econ. Entomol.* 1987, 80:1238–1245).

Although hydrogenation of the furan ring and the tigloyl group of salannin (1a) increased its antifeedant potency against the Colorado potato beetle, no difference in the antifeedant activity of salannin (1a) and 2',3',20,21,22,23-hexahydrosalannin (2a) was observed against the fall armyworm, Spodoptera frugiperda. By using cotton leaf disk choice bioassays (Klocke and Kubo, Entomol. Exp. Appl. 1982, 32:299–301), we found the $PC_{95}$ value for both 1a and 2a against S. frugiperda to be 75 μg. While the derivatives described and claimed herein will be effective against the insects which are sensitive to salannin, the effectiveness of salannin and its derivatives as antifeedants for various other species of insects should be determined empirically.

APPENDIX

Formula I
31a

| | $R_1$ | $R_2$ | $R_3$ |
|---|---|---|---|
| 1a | CH₃COO | HC=CCOO (3',2') with 4' H₃C, 5' CH₃ | CH₃ |
| 1b | OH | HC=CCOO (3',2') with 4' H₃C, 5' CH₃ | CH₃ |
| 1c | OH | OH | H |
| 1d | OH | OH | CH₃ |
| 1e | CH₃COO | CH₃CH₂CHCOO (4',3',2') with 5' CH₃ | CH₃ |
| 1f | CH₃O | HC=CCOO (3',2') with 4' CH₃, 5' CH₃ | CH₃ |
| 1g | CH₃O | OH | CH₃ |
| 1h | CH₃O | CH₃O | CH₃ |
| 1i | CH₃COO | CH₃COO | CH₃ |

Formula II
31b

| | $R_1$ | $R_2$ |
|---|---|---|
| 2a | CH₃COO | CH₃CH₂CHCOO (4',3',2') with 5' CH₃ |
| 2b | OH | OH |
| 2c | CH₃O | CH₃CH₂CHCOO (4',3',2') with 5' CH₃ |
| 2d | CH₃O | OH |
| 2e | CH₃O | CH₃O |
| 2f | H | CH₃CH₂CHCOO (4',3',2') with 5' CH₃ |

What is claimed:

1. 3-Deacetoxy-2',3',20,21,22,23,-hexahydrosalannin.
2. 3-O-Methyl-3-deacetyl-2',3',20,21,22,23-hexahydrosalannin.
3. 2',3',20,21,22,23-Hexahydrosalannin.
4. 1-Detigloyl-3-O-methyl-3-deacetyl-20,21,22,23-tetrahydrosalannin.
5. 1-Detigloy-3-deacetyl-20,21,22,23-tetrahydrosalannin.
6. 1,3-O-O-Dimethyl-1-detigloyl-3-deacetyl-20,21,22,23-tetrahydrosalannin.
7. 1,3-O-O-Dimethyl-1-detigloyl-3-deacetylsalannin.
8. 2',3'-Dihydrosalannin.
9. An insect antifeedant composition comprising an insect antifeedant effective amount of a 2',3',20,21,22,23-hexahydrosalannin derivative and an acceptable carrier.
10. An insect antifeedant composition comprising an insect antifeedant effective amount of a 20,21,22,23-tetrahydrosalannin derivative and an acceptable carrier.
11. An insect antifeedant composition comprising an insect antifeedant effective amount of 3-Deacetoxy-2',3',20,21,22,23-hexahydrosalannin and an acceptable carrier.
12. An insect antifeedant composition comprising an insect antifeedant effective amount of 3O-methyl-3-deacetyl-2'3',20,21,22,23-hexahydrosalannin and an acceptable carrier.
13. An insect antifeedant composition comprising an insect antifeedant effective amount of 2',3',20,21,22,23-Hexahydrosalannin and an acceptable carrier.
14. An insect antifeedant composition comprising an insect antifeedant effective amount of 1-Detigloyl-3-O-methyl-3-deacetyl-20,21,22,23-tetrahydrosalannin and an acceptable carrier.
15. An insect antifeedant composition comprising an insect antifeedant effective amount of 1-Detigloyl-3-deacetyl-20,21,22,23-tetrahydrosalannin and an acceptable carrier.
16. An insect antifeedant composition comprising an insect antifeedant effective amount of 1,3-O-O-Dimethyl-1-detigloyl-3-deacetyl-20,21,22,23-tetra-hydrosalannin and an acceptable carrier.
17. An insect antifeedant composition comprising an insect antifeedant effective amount of 1,3-O-O-Dimethyl-1-detigloyl-3-deacetylsalannin and an acceptable carrier.
18. An insect antifeedant composition comprising an insect antifeedant effective amount of 2',3'-dihydrosalannin and an acceptable carrier.

19. A method of decreasing feeding by an insect which comprises treating its environment with an insect antifeedant amount of a compound of claim 1.

20. A method of decreasing feeding by an insect which comprises treating its environment with an insect antifeedant amount of a compound of claim 2.

21. A method of decreasing feeding by an insect which comprises treating its environment with an insect antifeedant amount of a compound of claim 3.

22. A method of decreasing feeding by an insect which comprises treating its environment with an insect antifeedant amount of a compound of claim 4.

23. A method of decreasing feeding by an insect which comprises treating its environment with an insect antifeedant amount of a compound of claim 5.

24. A method of decreasing feeding by an insect which comprises treating its environment with an insect antifeedant amount of a compound of claim 6.

25. A method of decreasing feeding by an insect which comprises treating its environment with an insect antifeedant amount of a compound of claim 7.

26. A method of decreasing feeding by an insect which comprises treating its environment with an insect antifeedant amount of a compound of claim 8.

27. A method of decreasing feeding by an insect which comprises treating its environment with an insect antifeedant composition according to claim 9.

28. A method of decreasing feeding by an insect which comprises treating its environment with an insect antifeedant composition according to claim 10.

* * * * *